United States Patent

Nguyen

Patent Number: 6,102,878
Date of Patent: Aug. 15, 2000

[54] ADJUSTABLE SPLINT

[76] Inventor: Jimmy Phong Xuan Nguyen, 81 Childs Road, Chipping Norton, New South Wales, Australia, 2170

[21] Appl. No.: 09/270,268
[22] Filed: Mar. 16, 1999

[30] Foreign Application Priority Data

Sep. 15, 1998 [AU] Australia ................................. PP5937

[51] Int. Cl.[7] ........................................................ A61F 5/00
[52] U.S. Cl. .................................. 602/5; 602/20; 602/22
[58] Field of Search .................................... 602/5, 20, 21, 602/22; 128/878, 879, 880

[56] References Cited

U.S. PATENT DOCUMENTS

| 2,273,028 | 2/1942 | Eaton | 602/22 |
|---|---|---|---|
| 3,794,019 | 2/1974 | Ritland | 602/22 |
| 5,328,448 | 7/1994 | Gray | 602/22 |

FOREIGN PATENT DOCUMENTS 2501037  9/1982  France ...................................... 602/22

Primary Examiner—Michael A. Brown
Attorney, Agent, or Firm—Jacobson & Johnson

[57] ABSTRACT

There is an adjustable splint for fractures or other injuries of the figure or toe. The splint comprises an anchor plate adapted to be secured against the wearer's palm or sole by a velcro strap or the like, and a channel member which is engagable with apertures in the anchor plate at any one of a range of positions to align with the finger or toe fracture to be set. The channel portion is shaped to cradle and immobilize the finger or toe fracture and is pivotal relative to the anchor plate by a hinge. There are also apertures in the channel member for ventilation and to enable the fitting of a rest member to impose a degree of flexion onto the fracture during healing. There are hinge lines and breaking lines on the channel member to facilitate fitting to the finger or toe fracture.

9 Claims, 6 Drawing Sheets

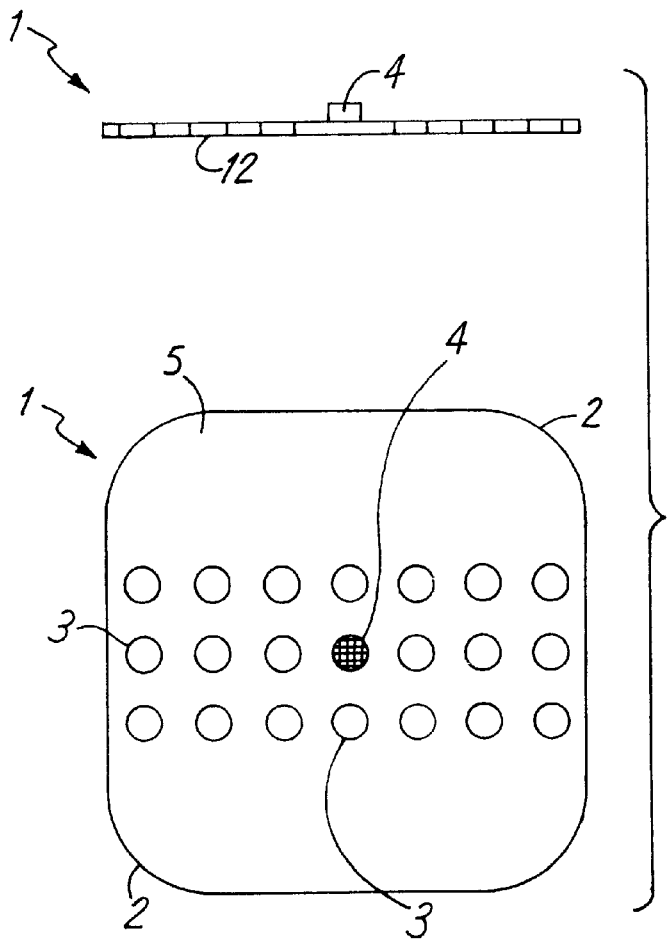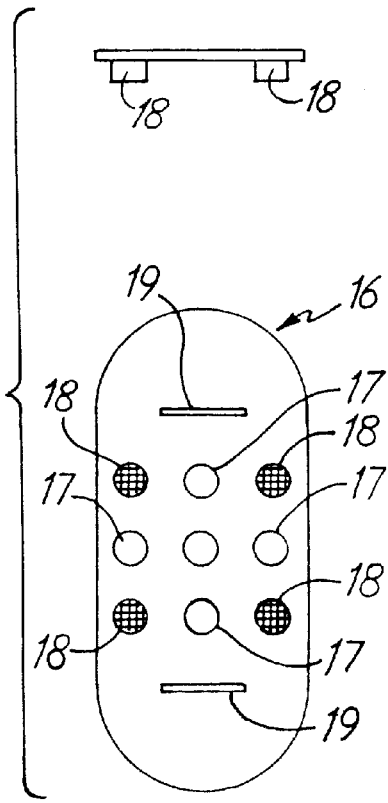

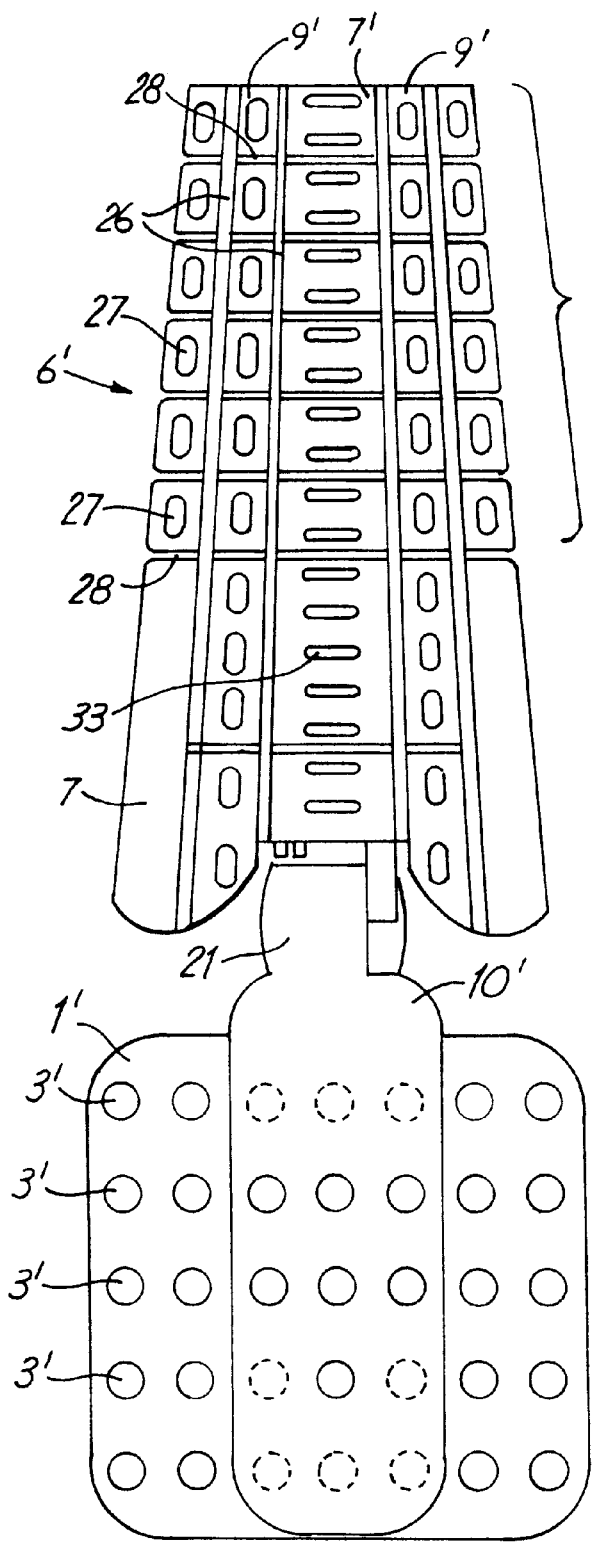
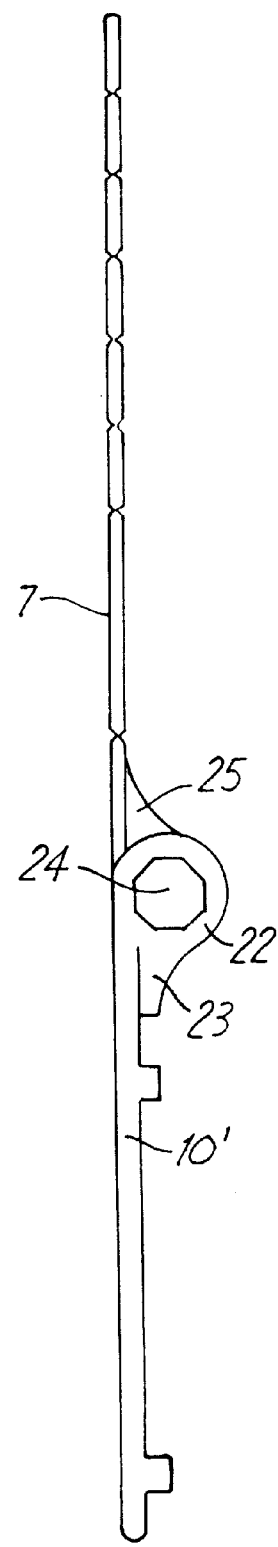
FIG. 5
FIG. 5A 6,102,878

ADJUSTABLE SPLINT

BACKGROUND OF THE INVENTION

This invention relates to medical apparatus. More particularly although not exclusively it discloses an improved adjustable splint for bone fractures, dislocations of joints, soft tissue injury and ligament ruptures of the fingers or toes.

Existing splints for the finger or toe typically comprise a strip of aluminium with a layer of foam padding on one side. The strip is folded lengthwise over one end and extends onto the palms. The device is then secured in place using tape or the like. Although the finger itself may be held reasonably straight by the splint there is little restraint against lateral movement. Also, due to the use of tape (elastoplaster) to secure the splint against the hand there is inadequate immobilisation and a certain amount of flexion and extension movement about the base of the finger can take place. As splints usually have to be in place for 2–4 weeks the use of tape or elastoplaster has several other disadvantages. For example it can cause skin allergic reactions due to the adhesive and sweating of the hand. The tape can fall off become dirty or develop an offensive odor. It can lose its adhesive properties after a few days especially if it gets wet by water or perspiration. For these reasons the tape adhesive is commonly replaced by the practitioner after several days of use and this increases the cost of maintaining the splint. During removal of the splint the adhesive property of the tape causes pain and discomfort for the wearer. For certain injuries such as dislocation and stable fracture it often recommended to allow the finger joint to mobilise several times a day to prevent stiffness. However the use of tape has often rendered this impractical and impossible without visits to the doctor to reapply the splint. The end of the aluminium strip protruding into the wearer's palm is also a source of discomfort and has been known to cause abrasion over the 2–4 weeks or so that the splint has to be worn. Prior art aluminum splints have to be cut to a suitable length using a "metal wire cutters" and have to be applied by a physician with the appropriate instruments. Further, the cost of these prior art splints is high. In addition to provision of the relatively expensive aluminium strip a layer of high quality foam padding has to be affixed along the inner side of the splint as a seperate step in manufacture.

In the applicant's earlier Australian patent applications a form of low cost one piece moulded splint is disclosed which overcomes many of the aforementioned disadvantages.

OBJECT OF THE INVENTION

It is an object of the present invention to provide further improvements in the form of a splint which is adjustable and reusable and can be assembled by a medical practioner, nurse or patient in any one of a range of configurations determined by the location of the fracture.

It is envisaged that this splint in emergency situations may even be applied prior to attending a doctors surgery.

SUMMARY OF THE INVENTION

Preferably said splint comprises an anchor plate for abutting the wearer's palm or sole and an elongated fracture support member, the support member being engagable with the anchor plate at any one of a range of positions so as to align with the particular fracture to be set.

BRIEF DESCRIPTION OF THE DRAWINGS

One currently preferred form of this invention will now be described with reference to the attached drawings in which:

FIG. 1 shows plan and end elevation views of the anchor plate component.

FIG. 4 shows plan and end elevation views of an adapter for the splint, FIGS. 5 and 5A slow plan and side views of a second embodiment of a splint according to this invention.

DETAILED DESCRIPTION OF PREFERRED EMBODIMENTS

Figure 2:
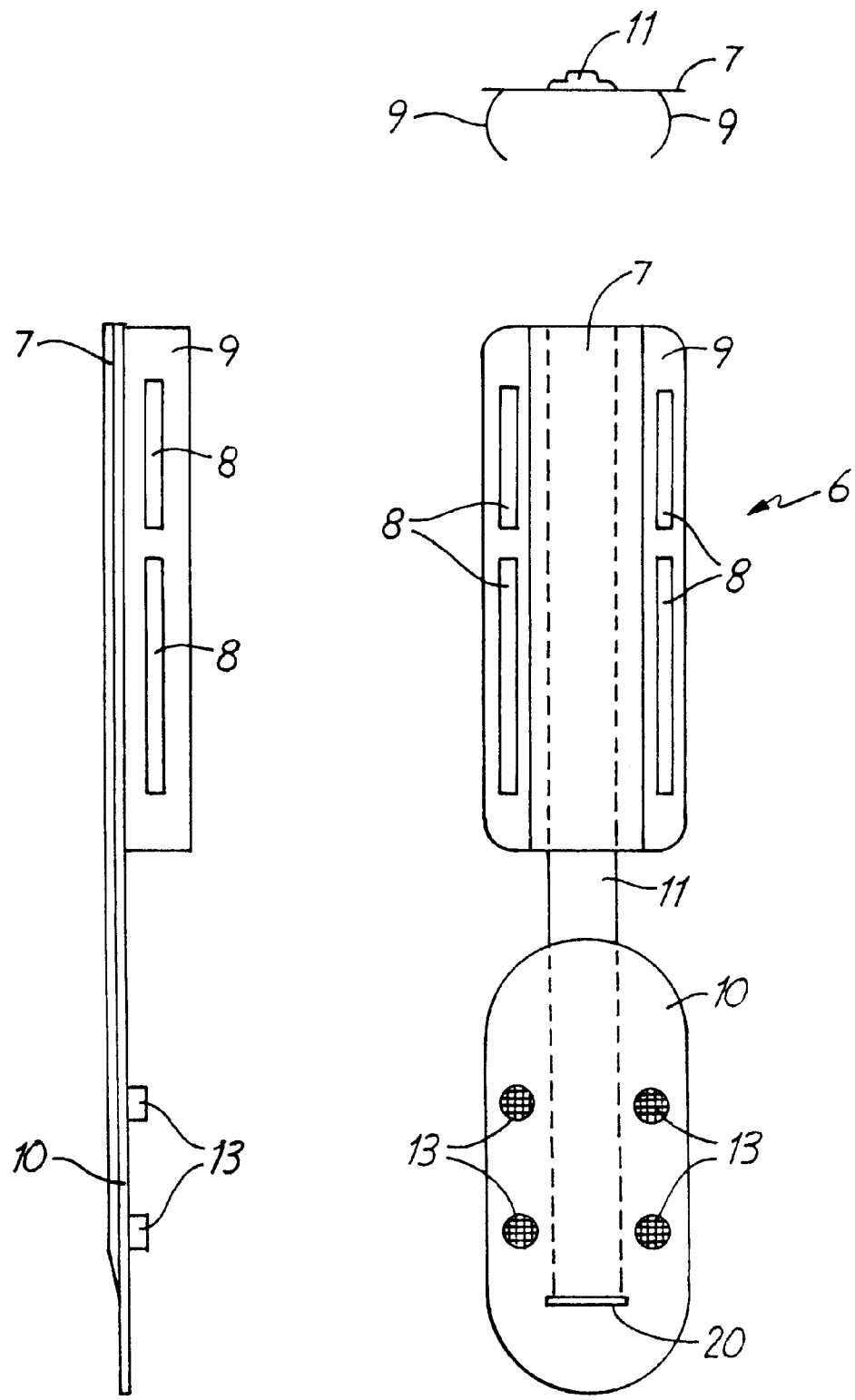
FIG. 2 shows plan and side elevation views of a fracture support component adapted for use with a finger.

Although these drawings depict the splint as applied to a finger fracture it could similarly within the scope of this invention be applied to a toe fracture.

Referring first to FIG. 1 the anchor plate (indicated generally as item 1) may be rectangular with rounded corners 2 to reduce abrasion on the wearer's palm or sole. Although with this embodiment the plate is about 70 mm square and 2 mm thick the invention extends to other sizes and shapes. Preferably the plate, as with the other components of the splint, is formed from any type of low cost and readily mouldable plastic such as Polypropylene. A series of apertures 3 are arranged in parallel rows across the width of the plate. There is also a central pin 4 extending from the upper face 5 of the plate.

Figure 3:
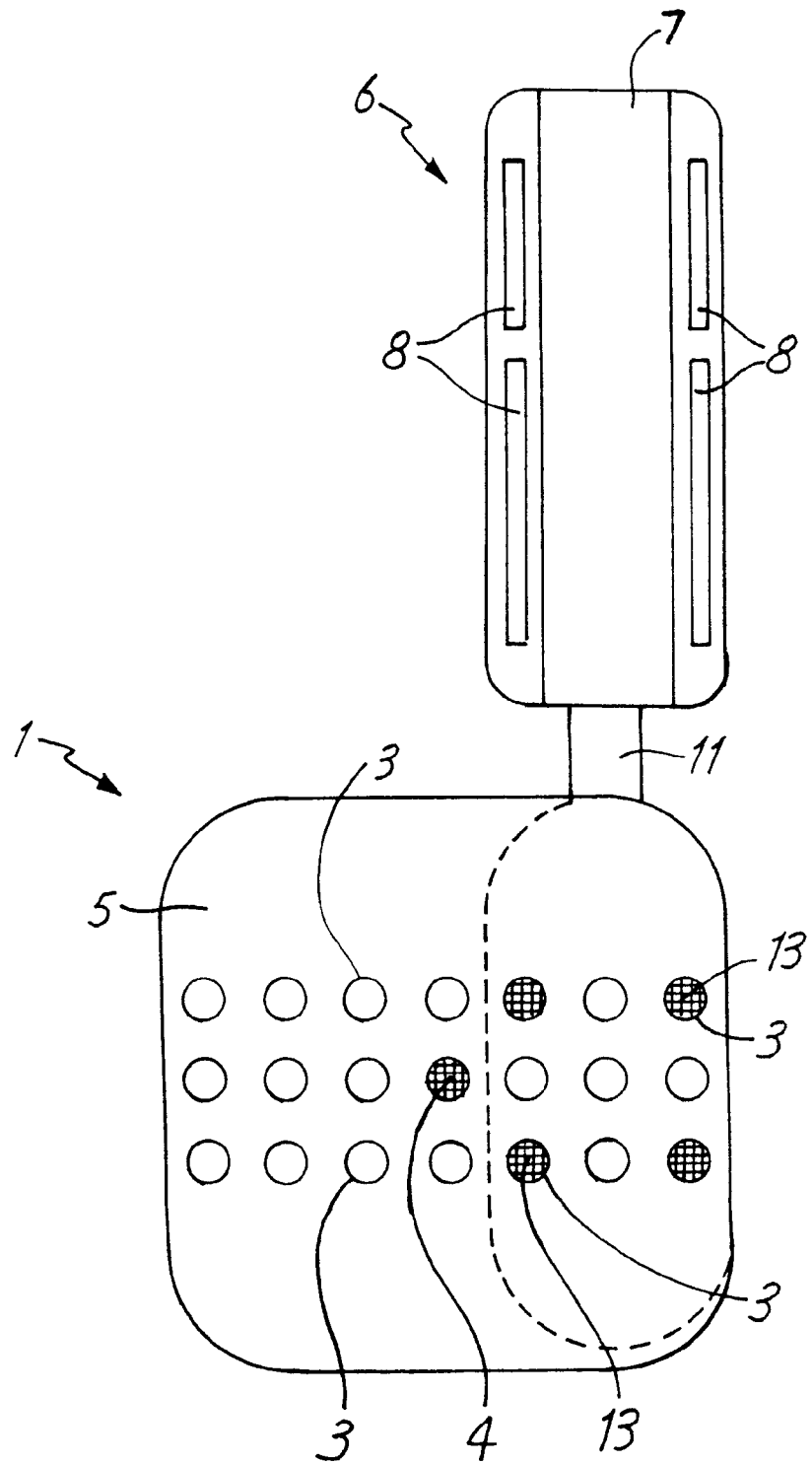
FIG. 3 shows the aforementioned splint components when assembled.

The fracture support member indicated generally as item 6 in FIG. 2 comprises an elongated channel portion 7 which with this embodiment is shaped to cradle the human finger. There are slots 8 formed in the sides 9 of this channel to receive one or more velcro fastering strips (not shown). These strips may be tightened as required to close the walls of the channel sufficiently to embrace the fracture and immobilise it. The use of velcro as opposed to close fitting adhesive tape has also been found to increase ventilation and reduce allergic reactions. The channel portion 7 is connected to a lower base portion 10 by means of a substantially rigid spine member 11. This lower portion 10 is adapted for a snap fit engagement onto the underside 12 of the anchor plate 1 as shown in FIG. 3. More specifically, it includes a set of four pins 13 which are shaped and positioned to press into corresponding sets of the apertures 3 in the anchor plate. While the support member 6 is shown by way of example here at the extreme right-band position, the repeating rows of apertures 3 in the anchor plate enable the support member to be fitted at any one of a range of positions across this plate in accordance with the location of the fractured finger. Although not shown in the drawings the underside 12 of the anchor plate 1 is clamped against the wearer's palm using any suitable form of tape or straps which extend around the hand and attach to the pin 4. Those apertures 3 which are not engaged by the pins 13 remain open for ventilation to increase wearer comfort.

As a further preferred feature of this invention a seperate adapter 16 as shown in FIG. 4 may be provided. This comprises a plate which may be similar in size and shape to the base portion 10 of the fracture support member described earlier. With this embodiment there are five apertures 17 formed in the adapter and four pins 18 as shown. It may thus be fitted onto the underside 12 of the anchor plate at various positions in a manner similar to that of the fracture support member 6. In this case however two parallel slots 19 are provided—one adjacent each end of the adapter. A length of malleable strip (not shown) may be fitted through these slots so that one end thereof would extend up to support the fracture in place of the substantially straight channel member 7 referred to earlier. Use of this adapter would allow a finger to be immobilised in a bent configuration as is sometimes required with such fractures. The unused apertures of the adapter together with those of the anchor plate would remain open for air ventilation.

Preferably the lower base portion 10 shown in FIG. 2 may also be provided with a strip receiving slot 20 to enable it to be used in the manner of an adapter when detached from the channel portion 7.

A second embodiment of a splint according to this invention is shown in FIG. 5 to 8. Here the main components that correspond in function to those of FIGS. 1 to 4 are marked by the same number but wish the addition of an accent ('). The anchor plate 1' is generally of the same shape and configuration as that of the first embodiment except that there are five rows of apertures 3' instead of the three shown in FIG. 3. The fracture support member 6' with this second embodiment also includes a mechanical hinge connection 21 between the channel portion 7' and the lower base portion 10' instead of the rigid spine of the first embodiment. This hinge preferably comprises a sleeve 22 attached to the base portion 10' by a ribs 23. The sleeve locates on an eight sided hinge pin 24 which attaches to the channel portion 7' by a second rib 25. The base portion 10' snap fits onto the underside of the anchor plate 1' in the same manner as with the first embodiment. The hinge however allows the fractured finger to be set by a physician at any desired angle to the palm 25A.

Figure 6:
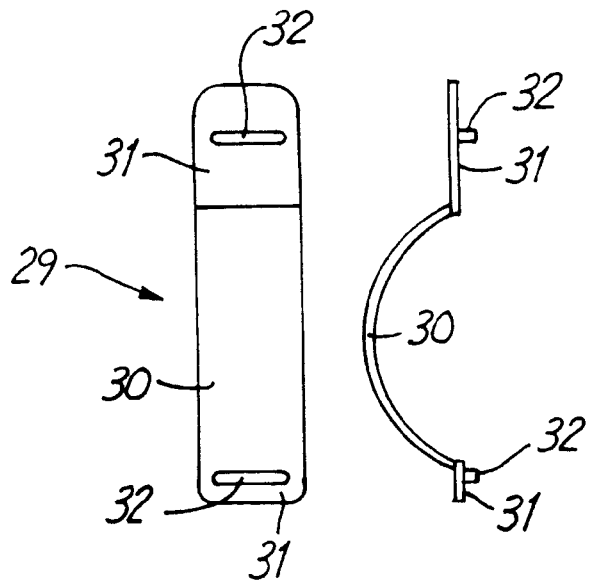
FIG. 6 shows plan and side views of a finger rest for use with the splint of FIG. 5.

There are a series of plastic hinge lines 26 extending along the length of the channel 7' on each side. These allow the sides 9' to be closely formed around and support different sized fingers. There are also a series of ventilation holes 27 in the sides 9'. To enable the channel 7' to be easily truncated to fit different finger lengths a series of break or cutting lines 28 may be formed transversely to its length. As a further improvement provision may also be made for imposing a predetermined flexion at any point along the length of a fractured finger. This as shown in FIG. 6 comprises a finger rest member 29 with a curved centre portion 30 and planar end portions 31. Each of these end portions includes ribs 32 which engage in a series of centrally located transverse slots 33 along the length of the bottom 7A of channel 7'. The rest member 29 may thus be snap fitted onto the channel 7' under any part of the finger to impose a preset degree of flexion during the healing process. As with the first embodiment the channel 7' would preferably be held in place around the finger and palm 25A using velcro or Polyurethane rubber straps 33A, 33B.

If required the end section A as shown in FIG. 5 may be broken off and used separately as a splint without the anchor plate 1'.

Figure 7:
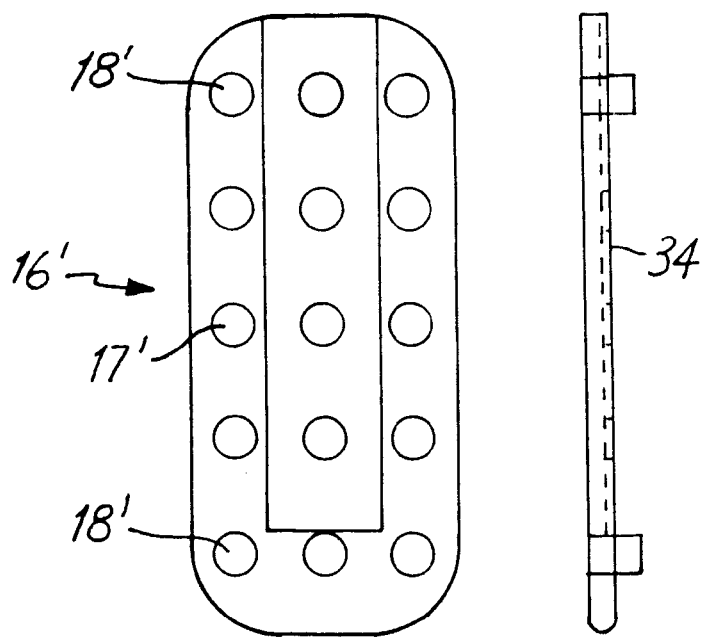
FIG. 7 shows plan and side views of a second form of adapter for use with the splint of FIG. 5.
Figure 8:
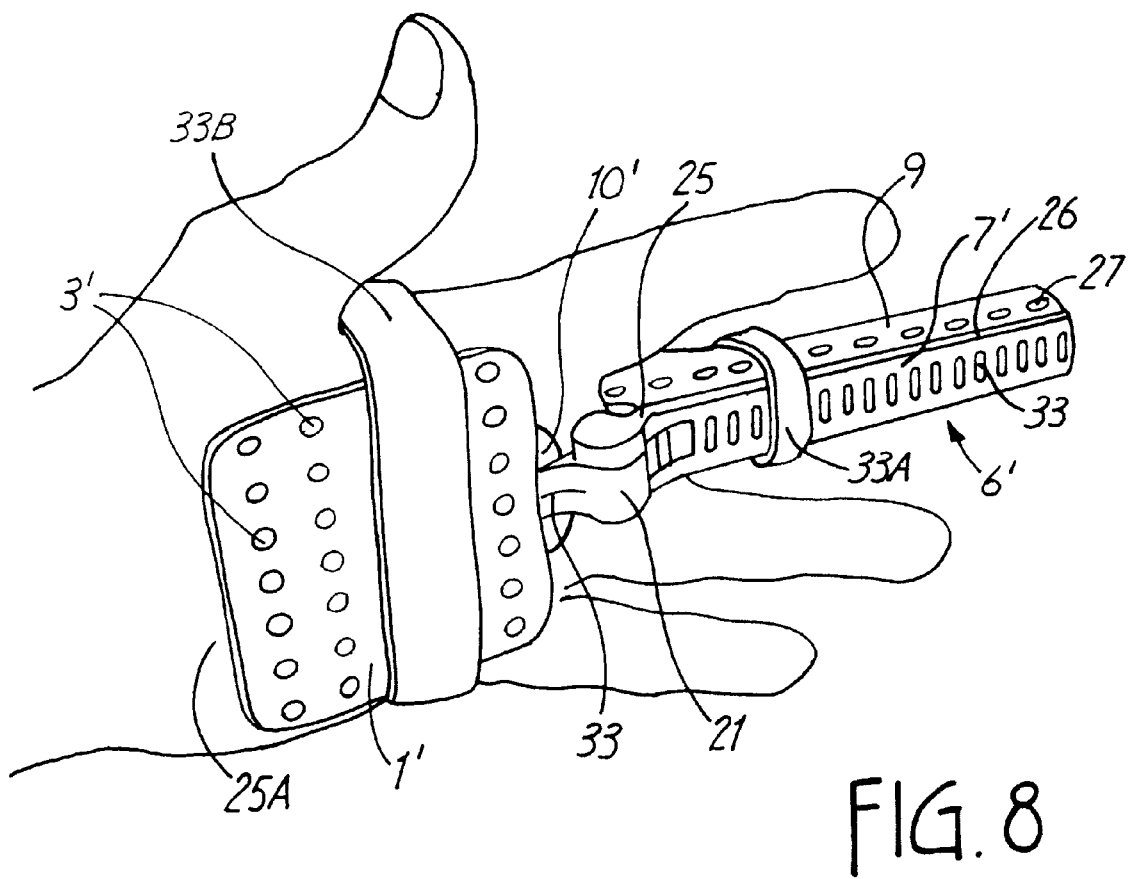
FIG. 8 shows an underside perspective view of the splint of FIG. 5 when fitted to a finger fracture.

A modified form of adapter 16' to enable a malleable strip to be fitted to the anchor plate 1' is shown in FIG. 7. The basic function here is the same as that of the adapter shown in FIG. 4. However a longitudinal slot 34 is now provided to receive the malleable strip. There is also five rows of apertures 17 and pins 18' to enable a snap fit onto the anchor plate 1' instead of three with the first embodiment.

It will thus be appreciated that this invention at least in the form of the embodiment described provides a novel and low cost adjustable splint for finger fractures. The advantages of this splint may be summarised as follows:

Practical

Water resistant

Non allergic

May be easily applied in emergency situations without the assistance of a medical personnel Provides immobilisation of both horizontal and vertical movement of joints and also the small bones of the hands to minimise pain and discomfort Provides better immobilisation of thumb and fifth digits due to the extra support from the base plate and the arrangement of the Velcro strapping system The splint adapter allows conventional aluminum strips to be used to immobilise a joint at an adequate flexion or extension angle.

Can be used to set multiple fractures at different flexion angles by fitting two support members 6' to an anchor plate 1'.

The use of strapping (e.g. Velcro) provides the following additional advantages:

Odorless

Splint can be removed and reapplied easily

Allows injured finger to be placed vertically on the support splint rather than pushed into a "U" shaped aluminium splint.

Removal is simple and painless as no adhesive is used

Because of increased comfort there would be less patient resistance to full term use of the splint.

Clearly however the example disclosed is only the currently preferred form of this invention and a wide variety of modifications may be made which would be apparent to a person skilled in the art. For example, the shape and configuration of the fracture support member and anchor plate may be changed according to design preference or to adapt the splint for use with toe fractures. Also, other means of connection between the splint components may be used within the scope of this invention.

Although not shown in the drawings foam is preferably applied to the side of the bass plate abutting the palm.

I claim:

1. An adjustable splint for fractures and other injuries of the finger or toe, said splint including an anchor plate adapted to be secured against a wearer's palm or sole and an elongated fracture support member which is engagable with said anchor plate at any one of a range of positions to align with the finger or toe fracture to be set, said elongated fracture support member comprising a channel portion which is shaped to cradle and immobilize said finger or toe fracture and a lower base portion having a set of pins which are shaped and positioned to press into corresponding sets of apertures repeating across said anchor plate to enable said base portion to engage with said anchor plate at said any one of a range of positions.

2. The adjustable splint as claimed in claim 1 wherein said channel portion is linked to said lower base portion by a mechanical hinge connection.

3. The adjustable splint as claimed in claim 2 wherein said mechanical hinge connection comprises a sleeve attached to the base portion by a first rib, said sleeve being securable at a selected one of a range of angular positions on a pin attached to said channel portion by a second rib.

4. The adjustable splint as claimed in claim 3 wherein a series of plastic hinge lines are formed along sides of the channel portion to allow said sides to be formed around said finger or toe fracture.

5. The adjustable splint as claimed in claim 4 wherein a series of transverse breaking or cutting lines are formed across said channel portion to enable said channel portion to be truncated to fit said finger or toe fracture.

6. The adjustable splint as claimed in claim 5 wherein a series of ventilation holes are formed in the sides of said channel portion.

7. The adjustable splint as claimed in claim 6 wherein a series of transverse slots are formed along the bottom of the channel member to enable a rest member to be snap fitted into said channel to impose a preset degree of flexion onto said finger or toe fracture during the healing process.

8. The adjustable splint as claimed in claim 7 wherein said anchor plate is rectangular with rounded corners.

9. The adjustable splint as claimed in claim 8 and including one or more hook and loop straps for holding said splint in place on the wearer's hand or foot.

* * * * *